US011376420B2

(12) United States Patent
De Kock et al.

(10) Patent No.: US 11,376,420 B2
(45) Date of Patent: Jul. 5, 2022

(54) TERMINAL TOOL FOR CONTINUOUS ELECTRICAL MONITORING DURING LEAD IMPLANT

(71) Applicant: Cardiac Pacemakers, Inc., St Paul, MN (US)

(72) Inventors: Andrew L. De Kock, Ham Lake, MN (US); G. Shantanu Reddy, Minneapolis, MN (US); Matthew J. Miller, Stillwater, MN (US); Kenneth Matrin Stein, Minneapolis, MN (US); Lili Liu, Maple Grove, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 134 days.

(21) Appl. No.: 16/744,893

(22) Filed: Jan. 16, 2020

(65) Prior Publication Data

US 2020/0222685 A1    Jul. 16, 2020

Related U.S. Application Data

(60) Provisional application No. 62/792,928, filed on Jan. 16, 2019.

(51) Int. Cl.
*A61N 1/04* (2006.01)
*A61N 1/39* (2006.01)
*A61N 1/37* (2006.01)

(52) U.S. Cl.
CPC .............. *A61N 1/048* (2013.01); *A61N 1/37* (2013.01); *A61N 1/3956* (2013.01)

(58) Field of Classification Search
CPC .. H01R 13/5224; H01R 2201/12; A61N 1/37; A61N 1/0595
See application file for complete search history.

(56) References Cited

U.S. PATENT DOCUMENTS 7,753,696 B2 * 7/2010 Hoecke .................. H01R 43/22
439/92

* cited by examiner

*Primary Examiner* — George R Evanisko
(74) *Attorney, Agent, or Firm* — Faegre Drinker Biddle & Reath LLP

(57) ABSTRACT

A terminal tool includes a main body, an electrical connector body, and an electrical connector. The main body includes a distal clamping section and a shaft. The shaft includes a window and a first lumen extending through the shaft for receiving a terminal end of an implantable lead. The electrical connector body includes a second lumen and is independently rotatable with respect to the main body. The shaft at least partially extends through the second lumen. The electrical connector is coupled to the electrical connector body and extends at least partially through the window of the shaft.

13 Claims, 12 Drawing Sheets

TERMINAL TOOL FOR CONTINUOUS ELECTRICAL MONITORING DURING LEAD IMPLANT

CROSS REFERENCE TO RELATED APPLICATION

This application claims priority to Provisional Application No. 62/792,928, filed Jan. 16, 2019, which is herein incorporated by reference in its entirety.

TECHNICAL FIELD

The present invention relates generally to implantable medical devices. More specifically, the present invention relates to devices, systems, and methods for installing and testing multi-conductor electrical leads within a patient's body.

BACKGROUND

Various types of medical electrical leads are used in cardiac rhythm management (CRM) and neurostimulation applications. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal, conductor end which contacts the heart tissue, and a proximal, terminal end which is connected to the pulse generator. The conductor end of the lead typically includes one or more features such as an active fixation helix or a number of passive tines to facilitate securing the lead to the heart tissue. The terminal end of the lead, in turn, includes one or more electrical contacts that are electrically connected to the electrodes on the terminal end of the lead via a number of conductors.

In certain applications, the leads are tested for proper positioning and function as part of the implantation process and prior to being connected to the pulse generator, allowing the implanting physician to evaluate pacing and sensing performance prior to concluding that the particular lead position is suitable. During the testing process, for example, a pacing system analyzer (PSA) may be connected to the terminal end of the lead to test the connection of the conductor end of the lead to the heart and/or to evaluate the performance of the lead. To facilitate connection of the PSA to the lead, a lead implant tool (or terminal tool) can be temporarily coupled to the terminal end of the lead, allowing the conductors of the PSA to be connected to the electrical contacts on the terminal end of the lead. In some cases, for example, the implant tool may facilitate the attachment of several alligator clips, plunger clips, or other spring-loaded clips to the electrical contacts on the terminal end of the lead.

SUMMARY

In Example 1, a terminal tool includes a main body, an electrical connector body, and an electrical connector. The main body includes a distal clamping section and a shaft. The shaft includes a window and a first lumen extending through the shaft for receiving a terminal end of an implantable lead. The electrical connector body includes a second lumen and is independently rotatable with respect to the main body. The shaft at least partially extends through the second lumen. The electrical connector is coupled to the electrical connector body and extends at least partially through the window of the shaft.

In Example 2, the terminal tool of Example 1, wherein the electrical connector body includes a proximal region, a distal region, and an electrical connection region positioned between the proximal region and the distal region, wherein the electrical connector is coupled to the electrical connector body at the electrical connection region.

In Example 3, the terminal tool of Example 2, wherein the proximal region and the distal region have larger outer diameters than the electrical connection region.

In Example 4, the terminal tool of any of Examples 1-3, wherein the electrical connector is configured to electrically couple to the terminal end of the implantable lead when the implantable lead is positioned within the terminal tool and while the main body is rotated with respect to the electrical connector body.

In Example 5, the terminal tool of any of Examples 1-4, wherein the electrical connector is rotationally fixed with the electrical connector body.

In Example 6, the terminal tool of any of Examples 1-5, wherein the shaft of the main body includes two or three windows.

In Example 7, the terminal tool of any of Examples 1-6, wherein the main body includes a proximal section, wherein the electrical connector body is positioned between the distal clamping section and the proximal section.

In Example 8, the terminal tool of any of Examples 1-7, wherein the shaft is integrally formed with the distal clamping section.

In Example 9, the terminal tool of any of Examples 1-8, wherein the electrical connector is independently rotatable with respect to the main body.

In Example 10, the terminal tool of any of Examples 1-9, further comprising a pin brake body coupled to the main body.

In Example 11, the terminal tool of any of Examples 1-10, further comprising a pin brake at least partially extending into the first lumen and arranged to receive the terminal end of the implantable lead.

In Example 12, the terminal tool of Example 11, wherein the pin brake body includes a hollow interior region, wherein the pin brake is at least partially positioned within the hollow interior region.

In Example 13, the terminal tool of any of Examples 11 and 12, wherein the pin brake and distal clamping section are configured to lock the helix in an extended position.

In Example 14, a terminal tool includes a main body and a conductive coil. The main body includes a distal clamping section, a proximal pin brake section, and an electrical connector section positioned between the distal clamping section and the proximal pin brake section. The electrical connector section includes a conductive ring with a lumen. The conductive coil is positioned at least partially within the lumen and mechanically and electrically coupled to the conductive ring.

In Example 15, a terminal tool includes a terminal tool body that extends between a proximal end and a distal end. The terminal tool body includes a lumen that extends between the distal end and the proximal end and is shaped to receive a terminal end of a lead. The terminal tool body includes an opening for receiving a terminal pin portion of the lead.

In Example 16, a terminal tool includes a main body, an electrical connector body, and an electrical connector. The main body includes a distal clamping section and a shaft.

The shaft includes a window and a first lumen extending through the shaft for receiving a terminal end of an implantable lead. The electrical connector body includes a second lumen and is independently rotatable with respect to the main body. The shaft at least partially extends through the second lumen. The electrical connector is coupled to the electrical connector body and extends at least partially through the window of the shaft.

In Example 17, the terminal tool of Example 16, wherein the electrical connector body includes a proximal region, a distal region, and an electrical connection region positioned between the proximal region and the distal region, wherein the electrical connector is coupled to the electrical connector body at the electrical connection region.

In Example 18, the terminal tool of Example 17, wherein the proximal region and the distal region have larger outer diameters than the electrical connection region.

In Example 19, the terminal tool of Example 16, wherein the electrical connector is configured to electrically couple to the terminal end of the implantable lead when the implantable lead is positioned within the terminal tool and while the main body is rotated with respect to the electrical connector body.

In Example 20, the terminal tool of Example 16, wherein the electrical connector is rotationally fixed with the electrical connector body.

In Example 21, the terminal tool of Example 16, wherein the shaft of the main body includes two or three windows.

In Example 22, the terminal tool of Example 16, wherein the main body includes a proximal section, wherein the electrical connector body is positioned between the distal clamping section and the proximal section.

In Example 23, the terminal tool of Example 16, wherein the shaft is integrally formed with the distal clamping section.

In Example 24, the terminal tool of Example 16, wherein the electrical connector is independently rotatable with respect to the main body.

In Example 25, the terminal tool of Example 16, further comprising a pin brake body coupled to the main body.

In Example 26, the terminal tool of Example 25, further comprising a pin brake at least partially extending into the first lumen and arranged to receive the terminal end of the implantable lead.

In Example 27, the terminal tool of Example 26, wherein the pin brake body includes a hollow interior region, wherein the pin brake is at least partially positioned within the hollow interior region.

In Example 28, the terminal tool of Example 26, wherein the pin brake and distal clamping section are configured to lock the helix in an extended position.

In Example 29, a terminal tool kit is disclosed as having component parts capable of being mechanically and electrically coupled for testing implantable leads. The terminal tool kit includes a main body with a distal clamping section, a proximal pin brake section, a spring conductor, a lumen through the main body, and an electrical connector section between the distal clamping section and the proximal pin brake section. The electrical connector section includes a conductive ring with an outer surface and an inner surface. The spring conductor is mechanically and electrically coupled to the inner surface of the outer conductive ring and at least partially positioned within the lumen. The terminal tool kit further includes a j-clip assembly for removably coupling to the main body. The j-clip assembly includes a j-shaped electrical connector configured to be mechanically coupled to the outer surface of the outer conductive ring and a spring plunger coupled to the j-shaped electrical connector for providing a force against the j-shaped electrical connector.

In Example 30, the terminal tool kit of Example 29, further comprising: an implantable lead configured to be slid into the lumen and configured to be electrically coupled to the j-shaped electrical connector via the spring conductor and the conductive ring when the j-shaped electrical connector is mechanically and electrically coupled to the outer surface of the outer conductive ring.

In Example 31, the terminal tool kit of Example 30, wherein the implantable lead includes a second lumen. The terminal tool kit further includes a stylet configured to be inserted into the second lumen and an electrical connector configured to be mechanically and electrically coupled to the stylet.

In Example 32, the terminal tool kit of Example 30, further comprising a pacing system analyzer to be electrically coupled to the implantable lead via the j-clip assembly, the conductive ring, and the spring conductor.

In Example 33, a terminal tool includes a main body with a distal clamping section, a proximal pin brake section, and an electrical connector section positioned between the distal clamping section and the proximal pin brake section. The electrical connector section includes a conductive ring with a lumen. The terminal tool includes a conductive coil positioned at least partially within the lumen and mechanically and electrically coupled to the conductive ring.

In Example 34, the terminal tool of Example 33, wherein the electrical connector section has a smaller outer diameter than the distal clamping section and the proximal brake section.

In Example 35, the terminal tool of Example 33, wherein the conductive ring has an outer diameter shaped to mechanically couple to a j-clip.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
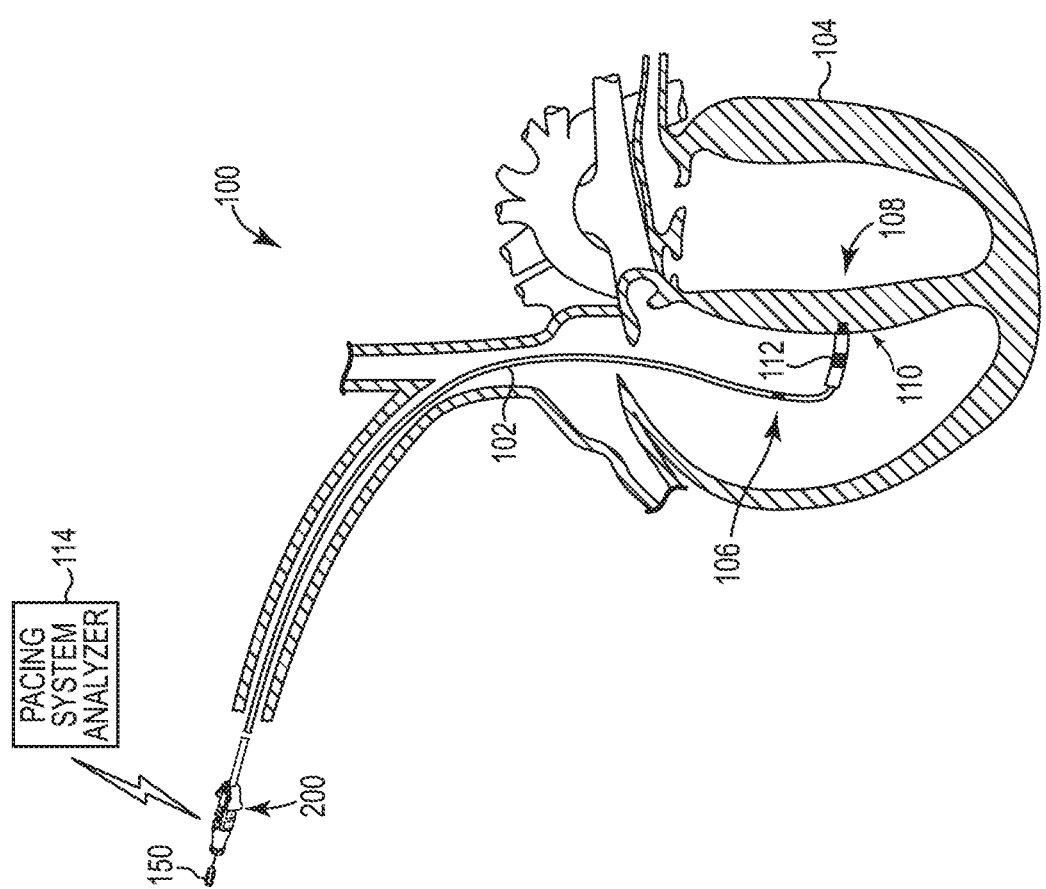
FIG. 1 is a schematic view showing a system for implanting and testing an implantable lead within a patient's body, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Certain embodiments of the present disclosure relate to implanting and testing multi-conductor electrical leads within a patient's body. When implanting a lead, physicians may extend and/or rotate the lead while affixing the distal end of the lead (e.g., a fixation helix) into tissue. During implantation of the lead, physicians periodically check the electrical activity sensed by the lead by connecting the lead to a PSA. This may involve, for example, coupling alligator clips between a terminal tool and the PSA. If physicians want to extend and/or rotate the lead, physicians will disconnect the alligator clips from the terminal tool to allow the lead to extend and/or rotate. If the physician wants to monitor the electrical activity sensed by the lead at different points during extension and/or rotation, the physician has to stop the extension or rotation to connect the alligator clips and then disconnect the alligator clips to continue extending or rotating the lead. This process adds time to the implantation procedure and does not allow electrical activity to be monitored continuously. Certain embodiments of the present disclosure are accordingly directed to methods and tools for allowing continuous monitoring of electrical activity during lead implantation.

FIG. 1 is a schematic view showing a system 100 for implanting and testing an implantable lead 102 within the body of a patient. For purposes of illustration and not limitation, the system 100 is described in conjunction with an implantable lead 102 for use in sensing cardiac electrical activity and/or for providing electrical stimulus therapy to a patient's heart 104. The system 100 can be used in other contexts where implantable leads are employed, and where testing is to be conducted prior to the connection of the lead to another implantable device such as a pulse generator. In certain embodiments, for example, the system 100 can be used to aid in the implantation and testing of an implantable neurostimulation lead prior to its connection to another implantable device such as a pulse generator.

A distal, conductive end 106 of the implantable lead 102 may be located as desired by an implanting physician within, on, or about the heart 104 of a patient. In the embodiment of FIG. 1, the conductive end 106 of the lead 102 is located in the heart 104 near an area 108 of the atrial septum or high ventricular septum. The conductive end 106 of the lead 102 includes one or more electrodes, including an electrically active fixation helix 110 and one or more ring electrodes 112. The fixation helix 110 and the ring electrode 112 are each coupled to a corresponding conductor within the lead 102, which during operation transmit electrical pulses back and forth between an implantable pulse generator (not shown) and the heart 104 for sensing cardiac activity and/or for providing pacing therapy to the heart 104. Although the distal end of the implantable lead 102 is shown in FIG. 1 as having a larger diameter, the distal end can be the same diameter as the rest of the implantable lead 102. In certain embodiments, the implantable lead 102 is a quadripolar lead that further includes a shocking coil or multiple shocking coils for providing shock therapy to the heart 104, although other types of leads can be used such as bipolar leads and multipolar leads. The type of pulse generator employed will vary based on the therapy to be performed. An example pulse generator can include a pacemaker, an implantable cardioverter defibrillator (ICD), a cardiac resynchronization therapy (CRT) device, or the like.

In the illustrative embodiment depicted, the system 100 further includes an implant tool 200 (shown in more detail in FIGS. 4-8 for one embodiment, FIG. 9 for another embodiment, and FIGS. 10-12 for another embodiment), a stiffening member such as a stylet or guidewire 202, and a Pacing System Analyzer (PSA) 114 that can be used for implanting and testing the lead 102 within the body. During the course of the procedure, to evaluate the viability of a potential fixation site, the function and location of the lead 102 can be tested by connecting a proximal, terminal end 116 of the lead 102 to the PSA 114. This evaluation can be performed prior to deploying the fixation helix 110 in the case of an active fixation lead and is then typically performed again after deploying the fixation helix 110. Such testing can be performed, for example, to verify that one or more contacts at the terminal end 116 of the lead 102 are in electrical contact with the fixation helix 110 and the ring electrode 112, and that the fixation helix 110 and the ring electrode 112 are properly positioned on or within the heart 104. The PSA 114 can also be used to perform other functions, such as programming the implantable device (e.g., pulse generator) to be coupled to the implantable lead 102, and to generate any pacing pulses necessary to support the patient during the implantation process.

The implant tool 200 is configured to permit the implanting physician to easily feed various stylets 202 into a pin lumen of the implantable lead 102. The implant tool 200 is configured to permit the implanting physician to make an electrical connection between the PSA 114 and a terminal pin 120 (shown in FIG. 2) and one or more terminal rings on the lead 102. In some embodiments, the implant tool 200 may be used with passive fixation leads to enable stylet passage and electrical connection while protecting the terminal connector.

In some embodiments, the implant tool 200 may be used to extend and/or retract the fixation helix 110 by attaching to the terminal pin 120 which, in turn, is connected to an internal driveshaft that connects to a fixation helix deployment mechanism. The driveshaft may or may not be electrically conductive, and the fixation helix 110 may or may not be electrically active. Moreover, other fixation mechanisms other than helical electrodes can also be deployed via the implant tool 200.

In some embodiments, the implant tool 200, stylet 202, and/or other components of the system 100 can be shipped as part of a kit already attached to an implantable lead 102. In certain embodiments, for example, the implant tool 200 can be pre-loaded onto a portion of the implantable lead 102 with the stylet 202 pre-inserted through the implant tool 200 and a portion of the lead 102. The pre-assembled components can then be packaged in a blister pack, pouch, or other suitable storage medium for later use and combination by the implanting physician.

The implant tool 200 is configured to provide a way to connect alligator clips or j-shaped clips or similar devices to terminal rings on the lead 102 without contacting the sensitive insulation components of the connector assembly and is configured to remain connected until connection of the device to another implantable device such as a pulse generator is to occur. At that time, the lead implant tool 200 is removed from the lead 102, and the lead 102 is then connected to the pulse generator. During normal operation, the lead 102 is configured to convey electrical signals back and forth between the pulse generator and the heart 104. For example, in those embodiments where the pulse generator is a pacemaker, the lead 102 can be used to deliver electrical therapeutic stimulus for pacing the heart 104. In those embodiments where the pulse generator is an ICD, the lead 102 can be utilized to deliver electric shocks to the heart 104 in response to an event such as a heart attack or ventricular tachycardia. In some embodiments, the pulse generator includes both pacing and defibrillation capabilities, or is capable of performing biventricular or other multi-site resynchronization therapies such as CRT. Example leads and lead connectors that can be used in conjunction with the implant tool 200 can include, but are not limited to, ICD leads (e.g., including a quadripolar, IS-1/DF-1 type connector), pacing and CRT leads (e.g., including an IS-4 or DF-4 quadripolar connector or IS-1 type connector), and pacing leads with sensing capabilities (e.g., a pressure sensing/pacing lead with a quadripolar type connector). Other types of leads and/or lead connector types can also be used in conjunction with the implant tool 200, as desired.

Figure 2:
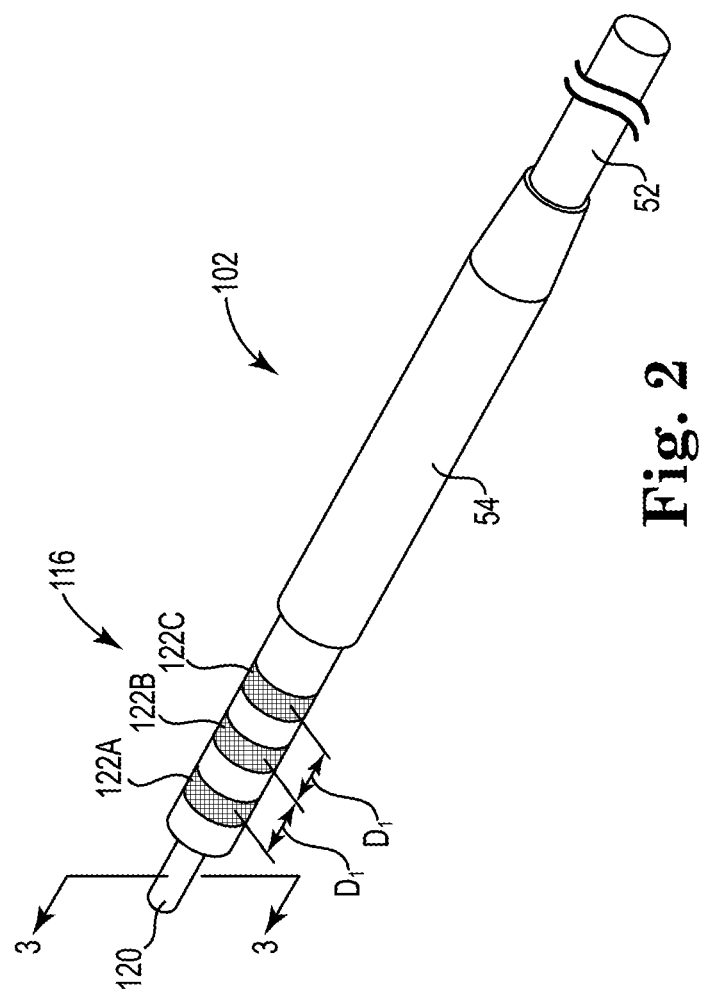
FIG. 2 is a perspective view showing a terminal end of an implantable lead, in accordance with certain embodiments of the present disclosure.

FIG. 2 is a perspective view showing the terminal end 116 of the implantable lead 102 of FIG. 1 in greater detail. As further shown in FIG. 2, the implantable lead 102 includes a lead terminal pin 120 and a number of terminal rings 122A-C each spaced axially apart from each other a distance along the length of the lead body 124. The terminal pin 120 is electrically coupled to the fixation helix 110 on the conductor end 116 and serves as a cathode for the implantable lead 102.

Although the implantable lead 102 includes a terminal pin 120 and three terminal rings 122A-C, in other embodiments the number and configuration of the terminal contacts may vary from that shown. In one embodiment, for example, the implantable lead 102 may be a bi-polar pacing lead including a single terminal pin and ring electrode. In other embodiments, the implantable lead 102 may be a CRT lead with four low-voltage electrodes. In one such embodiment, for example, the implantable lead 102 may be a single pass lead having two right ventricle electrodes and two right atrium electrodes. Other lead configurations are also possible.

Figure 3:
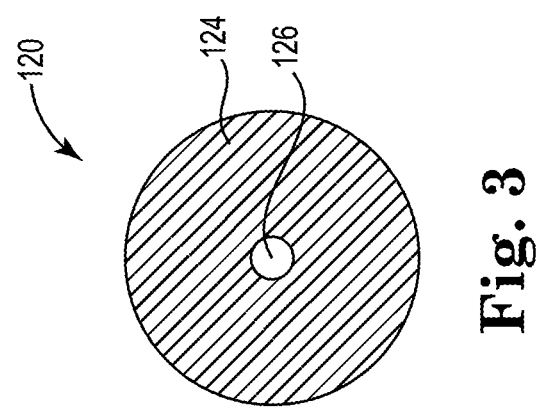
FIG. 3 is a cross-sectional view showing the implantable lead of FIG. 2.

FIG. 3 is a transverse cross-sectional view showing the terminal pin 120 of the implantable lead 102 of FIG. 2. As further shown in FIG. 3, and in some embodiments, the lead body 124 has a circular cross-sectional shape, and includes an enlarged-diameter terminal boot located distally of the terminal rings 122A-C. In certain embodiments, the terminal pin 120 includes a pin lumen 126 sized and shaped to allow various stylets or guidewires (such as stylet 150) to be inserted through the implantable lead 102 during the implantation procedure.

Figure 4:
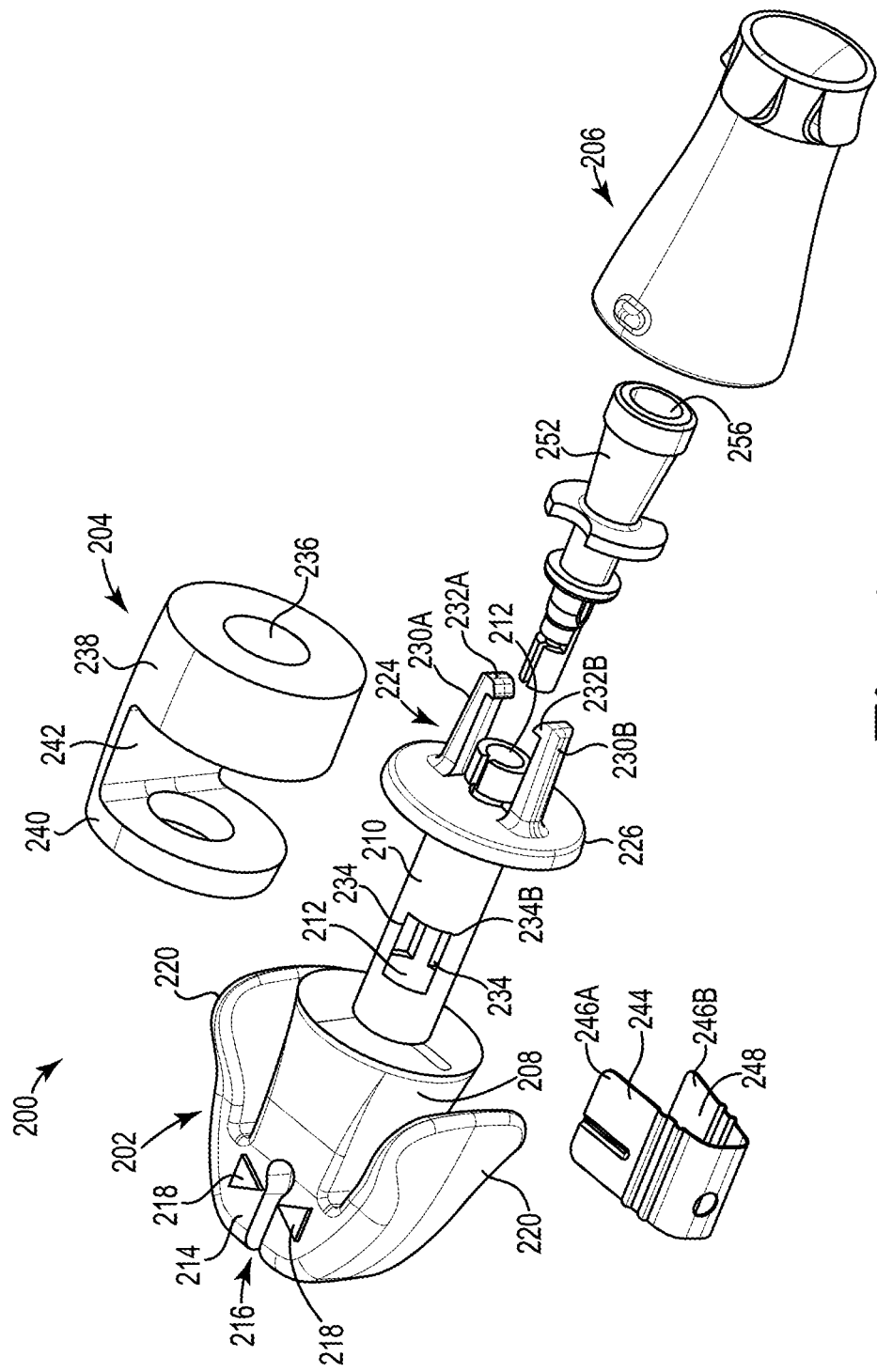
FIG. 4 is a perspective, exploded view of a terminal tool, in accordance with certain embodiments of the present disclosure.
Figure 5:
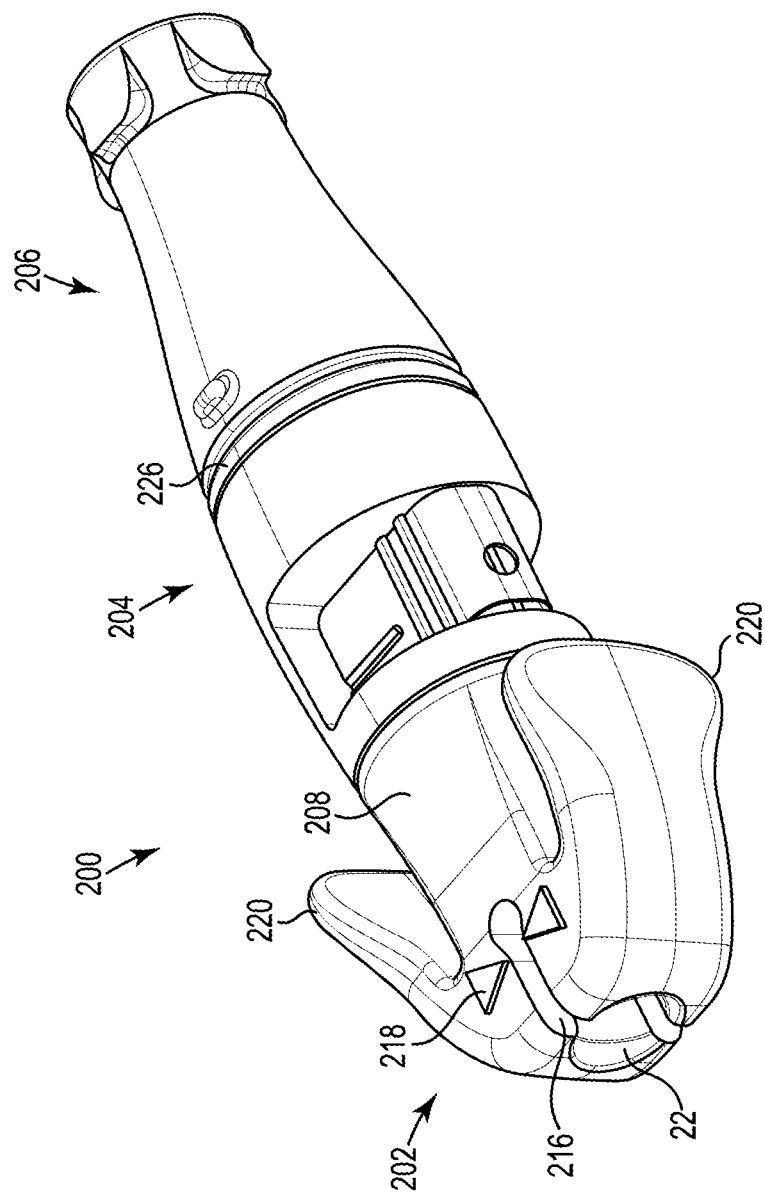
FIG. 5 is a perspective view of the terminal tool of FIG. 4 in its assembled form, in accordance with certain embodiments of the present disclosure.

FIGS. 4 and 5 are perspective views of the terminal tool 200. The terminal tool 200 includes a main body 202, an electrical connector body 204, and a pin brake body 206. The electrical connector body 204 is positioned between at least a portion of the main body 202 and the pin brake body 206.

The main body 202 has a boot grip portion 208 and a shaft 210. The boot grip portion 208 and the shaft 210 can be integrally formed together. In other embodiments, the shaft 210 is a separate component and extends through at least a portion of the boot grip portion 208. For example, boot grip portion 208 may be overmolded on and coupled to part of the shaft 210. The shaft 210 includes a lumen 212 extending the length of the shaft 210. The lumen 212 is sized to receive the terminal end 116 of the implantable lead 102.

Figure 7:
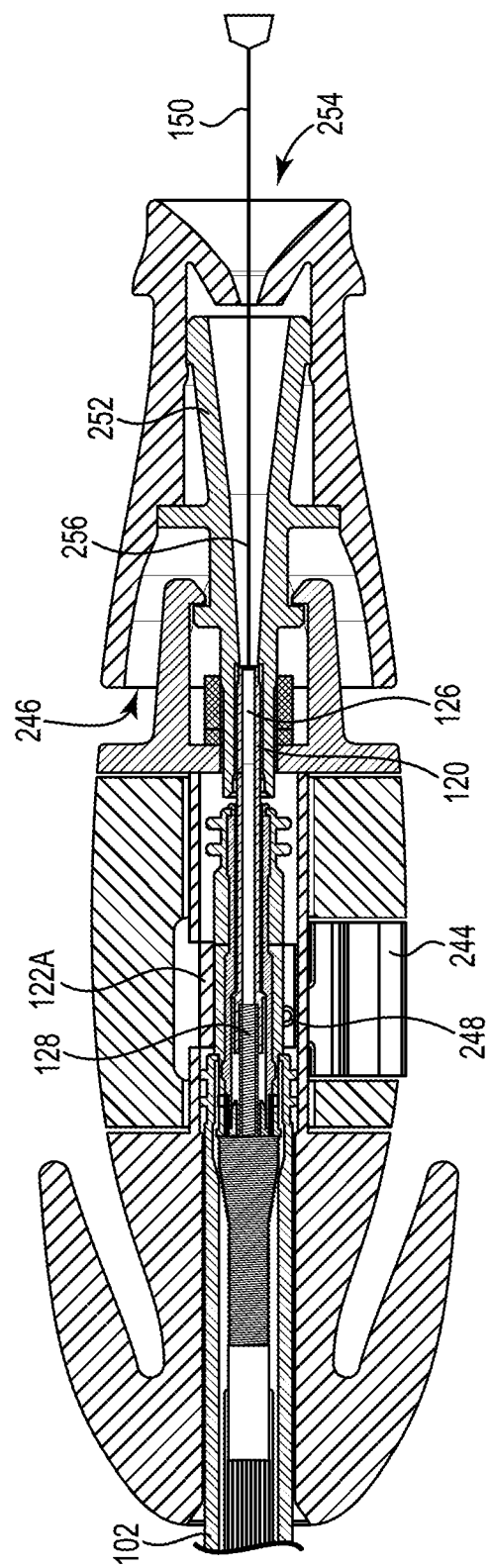
FIG. 7 is a sectional view of the terminal tool of FIGS. 4-6 with a lead at least partially positioned within the terminal tool, in accordance with certain embodiments of the present disclosure.
Figure 8:
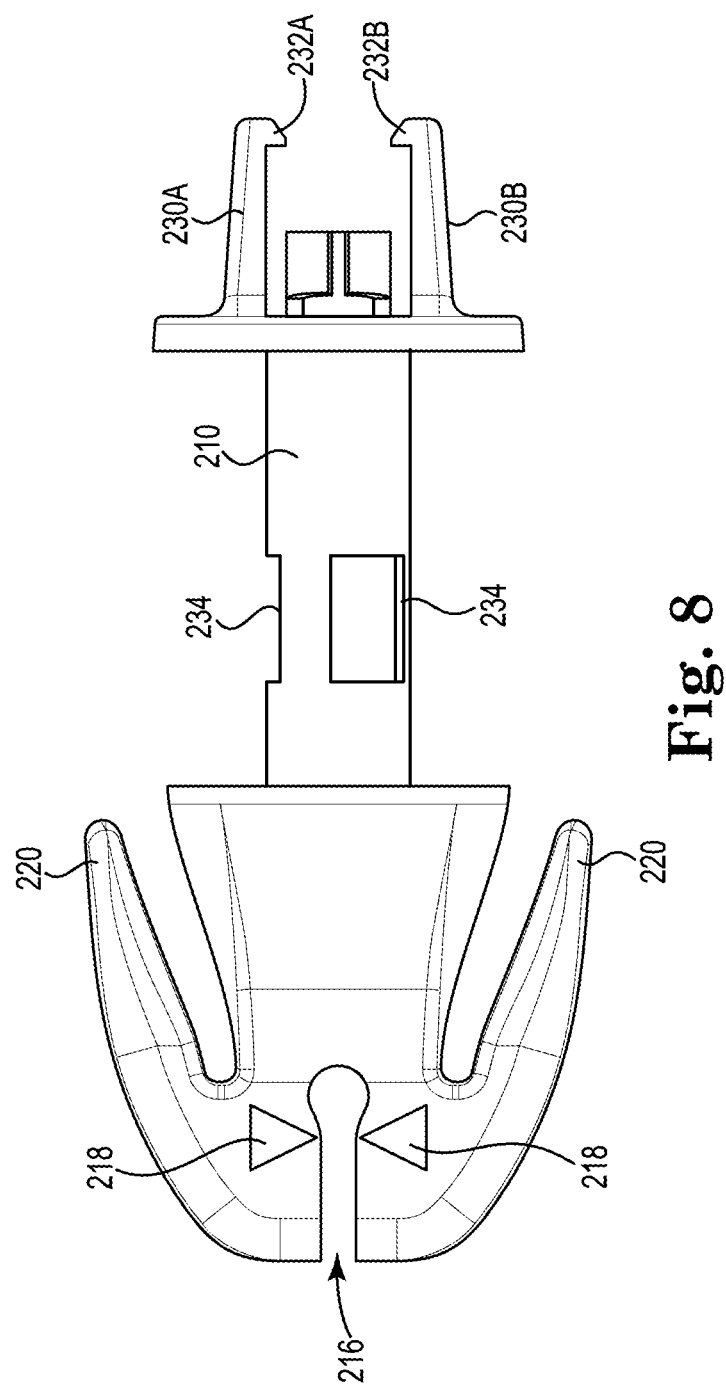
FIG. 8 is a side view of the distal section of the terminal tool of FIGS. 4-7, in accordance with certain embodiments of the present disclosure.

The boot grip portion 208 of the main body 202 includes a distal clamping section 214. The distal clamping section 214 includes a slot 216 and a number of indicator arrows 218 that provide the implanting physician with visual feedback that the terminal end 116 of the implantable lead 102 is properly inserted into the terminal tool 200. During insertion of the terminal end 116 into the lumen 212, the indicator arrows 218 are configured to align with a proximal end of the terminal boot 126 shown in FIG. 2. A number of levers 220 can be pushed together by the implanting physician to increase the diameter of an opening 222 of the lumen 212 slightly, allowing the terminal end 116 of the lead 102 to easily pass through the opening 222 and into the lumen 212. When engaged, the levers 220 provide a clamping force on the implantable lead 102, which as discussed further herein, counteracts the engagement force used to drive the fixation helix 120. The levers 220 also ensure that an adequate clamping force is applied to the terminal boot 126 regardless of the boot diameter. FIG. 7 shows the lead 102 with its terminal end 116 positioned in the terminal tool 200.

Once the proper positioning of the implantable lead 102 within the terminal tool 200 has been verified using the indicator arrows 220, the implanting physician then releases the levers 220, causing the size of the opening 222 to decrease slightly, thereby creating a friction fit between the boot grip portion 208 of the main body 202 and the terminal end 116 of the implantable lead 102. This friction fit is sufficient to prevent movement of the terminal tool 200 during implantation of the implantable lead 102 within the body.

Figure 6:
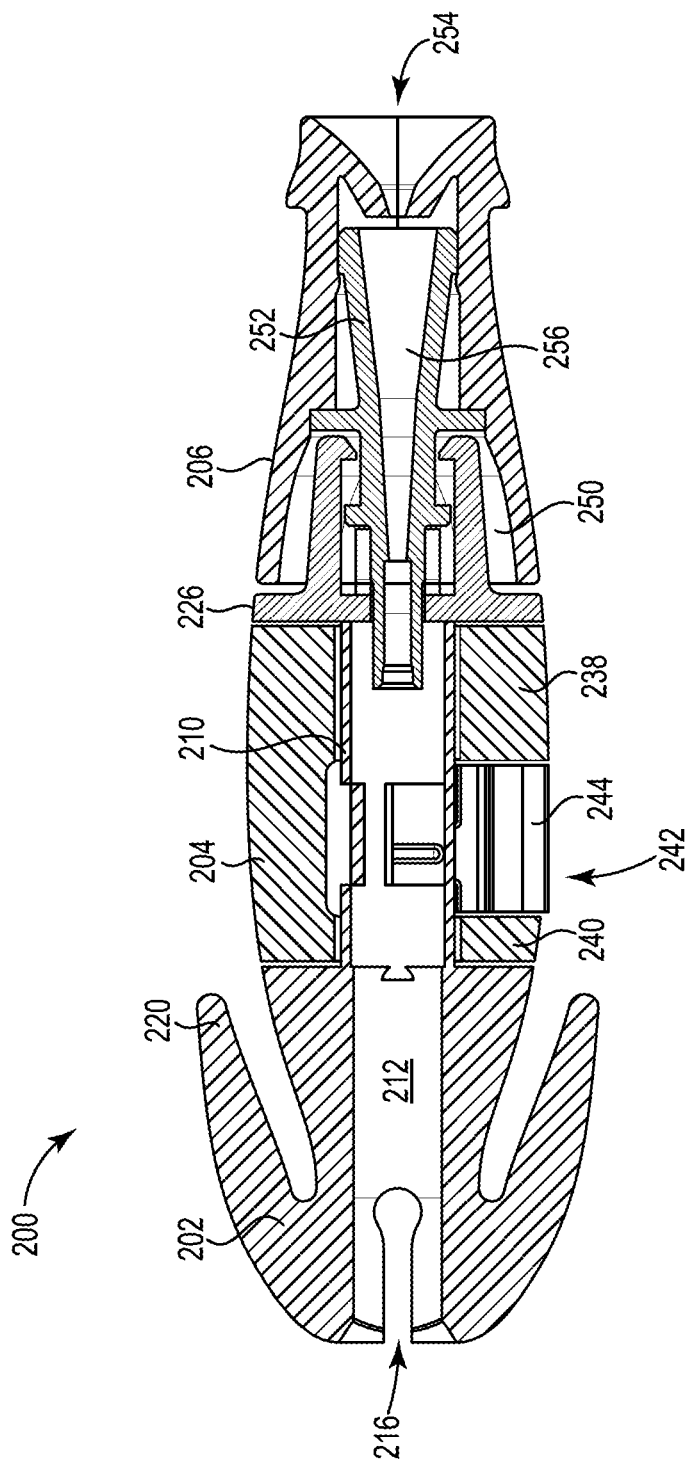
FIG. 6 is a sectional view of the terminal tool of FIGS. 4 and 5, in accordance with certain embodiments of the present disclosure.

As shown in FIG. 4, the main body 202 can include a proximal portion 224. The proximal portion 224 can include a disk-shaped section 226 and a clamping section 228. When the terminal tool 200 of FIGS. 4-8 is assembled, the electrical connector body 204 is positioned between the boot grip portion 208 and the disk-shaped section 226 and at least partially surrounds the shaft 210 as shown in FIGS. 5-7. The clamping section 228 of the proximal portion 224 can include one or more clamps 230A-B optionally with one or more teeth 232A-B. As shown in FIGS. 6 and 7, when the terminal tool 200 is assembled, the clamps 230A-B and teeth 232A-B help mechanically couple or maintain coupling between the main body 202 and components of the pin brake body 206.

The shaft 210 includes at least one window 234A-C, which will be described in more detail below as allowing mechanical and electrical contact between components of the terminal tool 200 and the lead 102. Although the windows 234A-C are shown as being rectangular shaped in FIGS. 4 and 8, the windows 234A-C can define other shapes.

The electrical connector body 204 includes a lumen 236, a proximal region 238, a distal region 240, and an electrical connection region 242 positioned between the proximal region 238 and the distal region 240. When the terminal tool 200 is assembled, the shaft 210 of the main body 202 extends through the lumen 236 of the electrical connector body 204. As such, the electrical connector body 204 can be rotated independently of the main body 202. As will be described in more detail below, having the electrical connector body 204 rotatable with respect to the main body 202 allows an implanting physician to rotate and/or extend the lead 102 during an implantation procedure while maintaining electrical communication between the lead 102 and the PSA 114. Maintaining electrical communication during implantation allows the physician to review the electrical activity sensed by lead 102 without interruption. Prior terminal tools required implanting physicians to electrically decouple the lead 102 from the PSA 114 to allow the terminal tool to be rotated when, for example, attaching a fixation helix to a patient's heart.

When the terminal tool 200 is assembled, an electrical contact 244 is positioned within the electrical connection region 242 and/or coupled to the electrical connector body 204. As shown in FIG. 4, the electrical contact 244 can have a U-shaped body. In certain embodiments, the electrical contact 244 is a spring-like clip that can be "pinched" together via an applied force. In certain embodiments, the electrical contact 244 comprises an electrically conductive metal such as MP35N, nickel-plated steel, nickel-plated beryllium copper, and the like. The electrical contact 244 can include features such as ridges to help provide a gripping surface for electrical connectors to mechanically coupled to the electrical contact 244.

During an implantation procedure, the electrical contact 244 is electrically coupled between the lead 102 and the PSA 114 so that the implanting physician can review, via the PSA 114, the electrical activity sensed by the lead 102. For example, an electrical connector such as an alligator clip can be mechanically and electrically coupled to the electrical contact 244, which is electrically and mechanically coupled to the lead 102, to facilitate electrical communication between the lead 102 and the PSA 114. FIG. 7 shows an example of the electrical contact 244 in contact with one of the terminal rings 122A. In certain embodiments, the connection via the electrical contact 244 is an electrical connection with an anode of the lead 102. An electrical connection with the lead's cathode can be created by mechanically and electrically coupling a separate electrical connector (e.g., alligator clip, j-shaped conductive clip or "j-clip") to the stylet 150. The stylet 150 is electrically coupled to an inner metal conductor coil 128 (shown in FIG. 7) of the lead 102.

When an electrical connector such as an alligator clip is coupled to the electrical contact 244, the electrical connector provides an the inwardly-directed force that causes ends 246A and 246B of the electrical contact 244 to move toward each other which, in turn, causes interior portions 248 of the electrical contact 244 to extend through one or more windows 234A-C of the shaft 210 and contact the corresponding terminal ring 122A-C of the lead 102.

With the electrical connectors respectively coupled between the PSA 114 and the electrical contact 244 and the stylet 150, the implanting physician may view the electrical activity sensed by the lead 102. As mentioned above, because the main body 202 and the electrical connector body 204 can rotate independently of each other, the implanting physician can view the electrical activity sensed by the lead 102 while the lead is being rotated and/or extended via the terminal tool 202 because the electrical connectors do not need to be removed during rotation. As such, the implanting physician can view the electrical activity sensed by the lead 102 during the process of attaching the fixation helix 110 to the heart 104 via rotation and/or extension of the lead 102 (and therefore the fixation helix 110).

The pin brake body 206 includes a hollow interior region 250 in which a pin brake 252 is at least partially positioned when the terminal tool 200 is assembled. The pin brake body 206 also includes an opening 254 for allowing the stylet 150 to be moved into and out of the terminal tool 200. The pin brake 252 includes a lumen 256 also for allowing the stylet 150 to be moved into and out of the terminal tool 200. During an implant procedure, the pin brake body 206 and pin brake 252 can be used to rotatably engage the terminal pin 120 of the lead 102 when attaching the fixation helix 110 within the heart tissue. For example, the pin brake body 206 and pin brake 252 can lock the lead 102 in its fully extended position. In such embodiments, the main body 202, the pin brake body 206, and the pin brake 252 are fixed relative to each other and rotate together independently of the electrical connector body 204.

Figure 9:
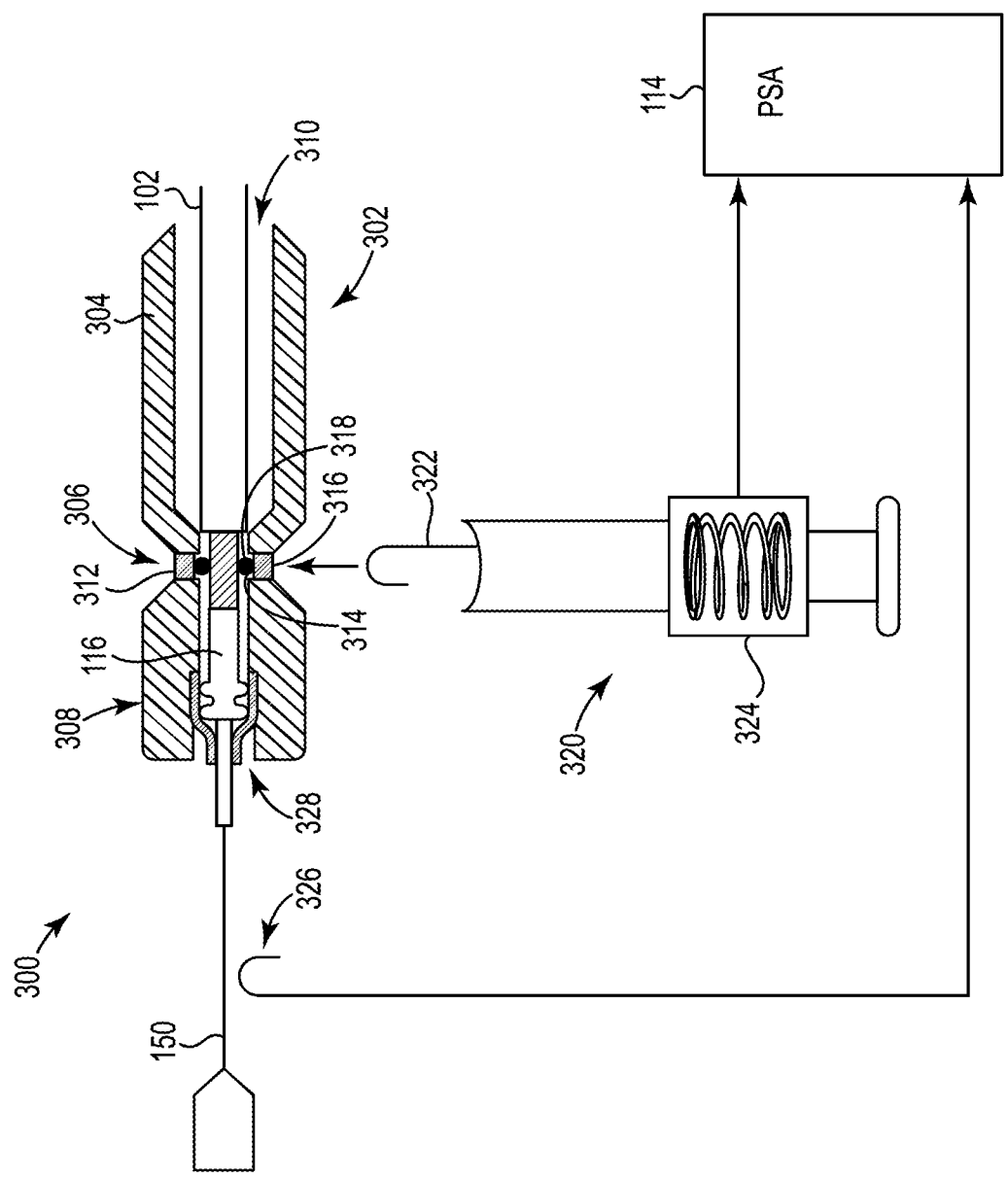
FIG. 9 shows a schematic of a system or kit including a terminal tool, in accordance with certain embodiments of the present disclosure.

FIG. 9 shows a system and/or components of a kit that includes a terminal tool 300 with a main body 302. The main body 302 includes a distal clamping section 304, an electrical connector section 306, and a proximal pin brake section 308. The electrical connector section 306 is positioned between the distal clamping section 304 and the proximal pin brake section 308. In certain embodiments, the distal clamping section 304, the electrical connector section 306, and the proximal pin brake section 308 are fixed to each other such that the sections are not independently rotatable with respect to each other.

Like the terminal tool 200 of FIGS. 4-8, the main body 302 can include distal clamping section with a slot and indicator arrows that provide the implanting physician with visual feedback that the terminal end 116 of the implantable lead 102 is properly inserted into the terminal tool 300. During insertion of the terminal end 116 into a lumen 310 of the main body 302, the indicator arrows 314 are configured to align with a proximal end of the terminal boot 126 shown in FIG. 2. The distal clamping section can include levers to be pushed together by the implanting physician to increase the diameter of an opening of the lumen 310, allowing the terminal end 116 of the lead 102 to easily pass into the lumen 310.

The electrical connector section 306 includes a conductive ring 312 that is cylinder- or ring-shaped with an inner surface 314 and an outer surface 316. The inner surface 314 of the conductive ring 312 forms a portion of the lumen 310 that receives the implantable lead 102. The outer surface 316 of the conductive ring 312 is shaped to receive a j-clip, which is described in more detail below.

A conductive coil 318 is mechanically and electrically coupled to the inner surface 314 of the conductive ring 312. As such, the conductive coil 318 is positioned within the lumen 310. The conductive coil 318 may be considered to be a coiled spring having its ends joined together to form an annular shape. As the implantable lead 102 rotates within the terminal tool 300, the lead 102 remains electrically coupled to the conductive ring 312 via the conductive coil 318. As such, the lead 102 can be rotated within the terminal tool 300 without rotating the conductive ring 312. Like the terminal tool 200 of FIGS. 4-8, electrical communication between the lead 102 and the PSA 114 can be maintained during rotation of the lead 102.

FIG. 9 also shows an electrical connection assembly 320 including a conductive j-clip portion 322. During an implantation procedure, the electrical connection assembly 320 can be electrically coupled between the lead 102 (via the conductive coil 318 and the conductive ring 312) and the PSA 114. The j-clip portion 322 is sized and arranged to mechanically and electrically couple to the outer surface 316 of the conductive ring 312. The j-clip portion 322 is mechanically coupled to one or more springs or spring plungers 324. The spring plunger 324 helps maintain a force (e.g., a pulling force) against the j-clip portion 322 so that the j-clip portion 322 does not decouple from the conductive ring 312.

Another electrical connection can be made between the PSA 114 and the lead 102 via a j-clip 326 that is mechanically and electrically coupled to the stylet 150, which is electrically coupled to the lead 102. The j-clip 326 is electrically coupled between the lead 102 and the PSA 114.

As shown in FIG. 9, the terminal tool 300 can include a pin brake 328 that secures to the terminal end 116 of the lead 102 and that can be manipulated to rotate the lead 102.

In certain embodiments, the terminal tool 300, the electrical connection assembly 320, the implantable lead 102, the j-clip 326, and/or the PSA 114 are provided as a kit. For example, the kit may include the electrical connection assembly 320 with the j-clip portion 322 that is sized to fit around the conductive ring 312 of the terminal tool 300 but that, in kit form, is not mechanically coupled to the conductive ring 312. The components of the kit can be assembled and/or coupled together as described above to carry out an implantation procedure.

Figure 10:
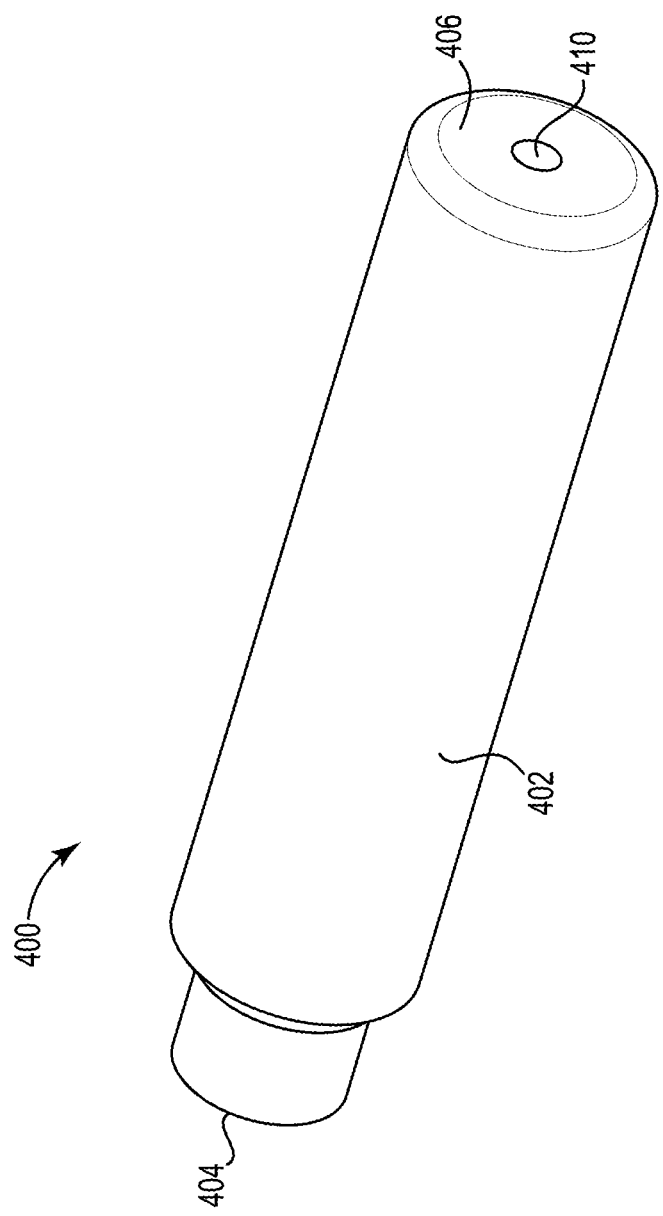
FIG. 10 is a perspective view of a terminal tool, in accordance with certain embodiments of the present disclosure.
Figure 11:
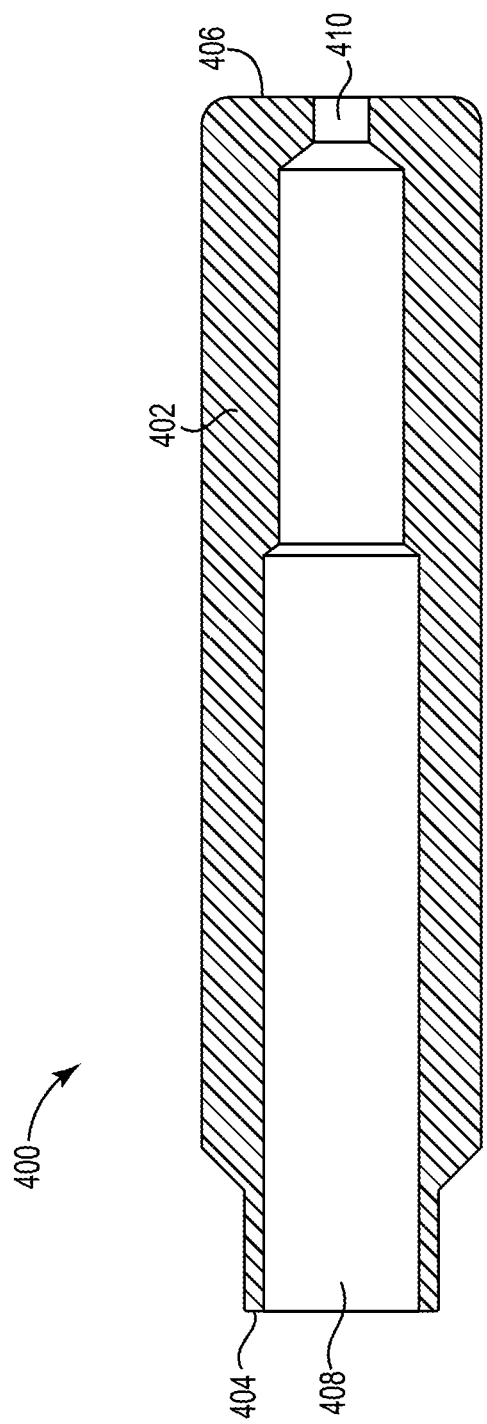
FIG. 11 is a sectional view of the terminal tool of FIG. 9, in accordance with certain embodiments of the present disclosure.
Figure 12:
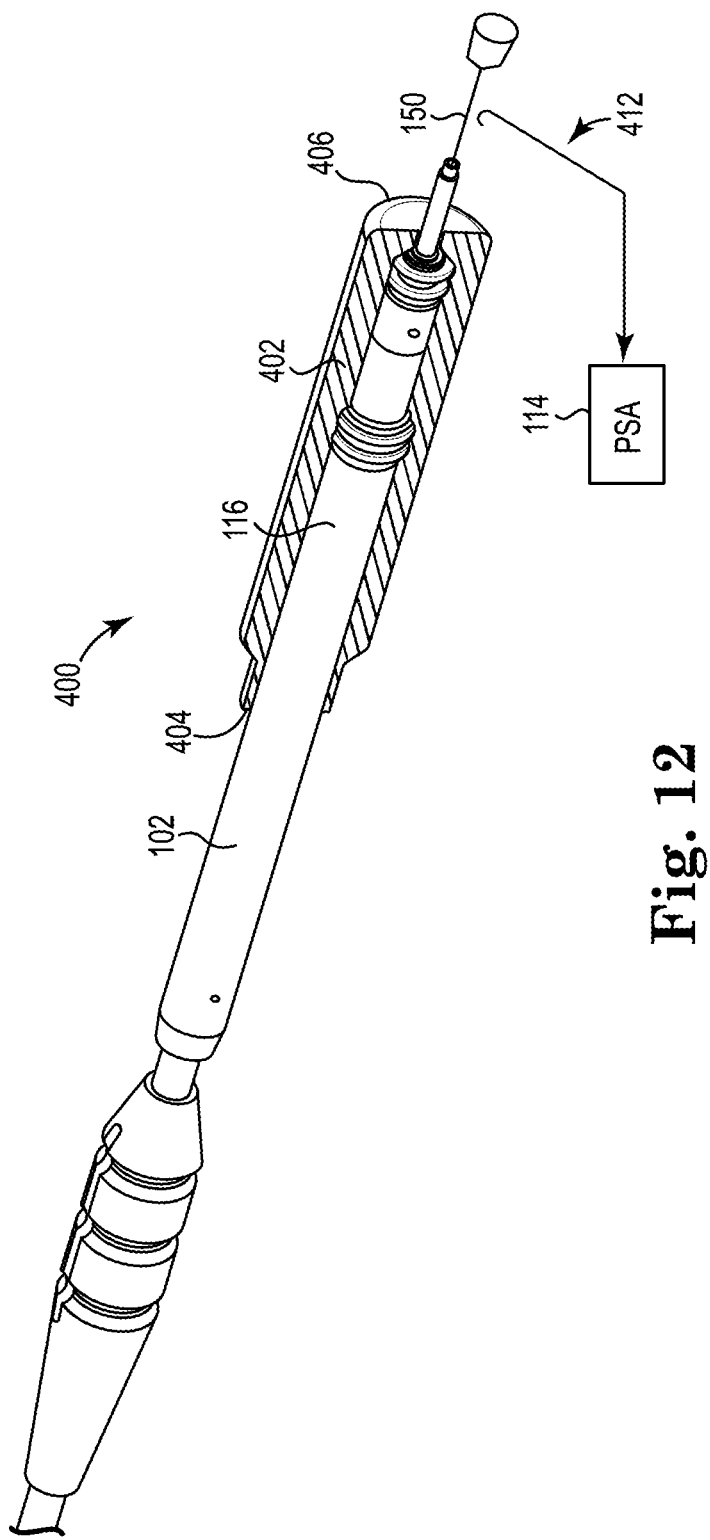
FIG. 12 is a schematic of a system or kit showing a sectional view of the terminal tool of FIGS. 9 and 10 with a lead at least partially positioned within the terminal tool, in accordance with certain embodiments of the present disclosure.

FIGS. 10-12 show various aspects a terminal tool 400, the lead 102, the stylet 150, and the PSA 114, with FIG. 12 showing the lead 102 at least partially positioned within the terminal tool 400. Components such as the terminal tool 400 and the lead 102 can be provided as a kit that is assembled or otherwise coupled together for use during an implantation procedure.

The terminal tool 400 has a terminal tool body 402 extends between a proximal end 404 and a distal end 406 and can be cylindrical shaped. The terminal tool 402 includes a lumen 408 that extends between the distal end 406 and the proximal end 404. The lumen 408 can be shaped to accommodate different shapes and sizes of the lead 102. The terminal tool body 402 can comprise a non-conductive material and be constructed of a single piece of such material. During an implantation procedure, the terminal tool 400 is slid over the terminal end 116 of the lead 102 such that the terminal pin 120 extends through an opening 410 at the distal end 406. In certain embodiments, the opening 410 is smaller in diameter than the lumen 408. The terminal tool 400 can be used to lock the terminal pin 120 to allow an implanting physician to fix the fixation helix 110 of the lead 102.

A j-clip 412 can be electrically coupled between the lead 102 and the PSA 114. For example, the j-clip 412 can be mechanically and electrically coupled to the stylet 150, which is electrically coupled to the lead 102. In such an arrangement, the electrical connection is made with the lead's 102 cathode.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A terminal tool comprising:
a main body including a distal clamping section and a shaft, the shaft including a window and including a first lumen extending through the shaft for receiving a terminal end of an implantable lead;
an electrical connector body including a second lumen and independently rotatable with respect to the main body, wherein the shaft at least partially extends through the second lumen; and
an electrical connector coupled to the electrical connector body and extending at least partially through the window of the shaft.

2. The terminal tool of claim 1, wherein the electrical connector body includes a proximal region, a distal region, and an electrical connection region positioned between the proximal region and the distal region, wherein the electrical connector is coupled to the electrical connector body at the electrical connection region.

3. The terminal tool of claim 2, wherein the proximal region and the distal region have larger outer diameters than the electrical connection region.

4. The terminal tool of claim 1, wherein the electrical connector is configured to electrically couple to the terminal end of the implantable lead when the implantable lead is positioned within the terminal tool and while the main body is rotated with respect to the electrical connector body.

5. The terminal tool of claim 1, wherein the electrical connector is rotationally fixed with the electrical connector body.

6. The terminal tool of claim 1, wherein the shaft of the main body further includes a second window.

7. The terminal tool of claim 1, wherein the main body includes a proximal section, wherein the electrical connector body is positioned between the distal clamping section and the proximal section.

8. The terminal tool of claim 1, wherein the shaft is integrally formed with the distal clamping section.

9. The terminal tool of claim 1, wherein the electrical connector is independently rotatable with respect to the main body.

10. The terminal tool of claim 1, further comprising:
a pin brake body coupled to the main body.

11. The terminal tool of claim 10, further comprising:
a pin brake at least partially extending into the first lumen and arranged to receive the terminal end of the implantable lead.

12. The terminal tool of claim 11, wherein the pin brake body includes a hollow interior region, wherein the pin brake is at least partially positioned within the hollow interior region.

13. The terminal tool of claim 11, wherein the pin brake and distal clamping section are configured to lock a helix in an extended position.

* * * * *